United States Patent [19]

Rowlands

[11] 4,159,337
[45] Jun. 26, 1979

[54] TREATMENT OF HELMINTH INFECTIONS WITH OXFENDAZOLE AND DIAMPHENETHIDE, AND COMPOSITIONS THEREFOR

[75] Inventor: Dewi T. Rowlands, Berkhamsted, England

[73] Assignee: Burroughs Wellcome Co., Research Triangle Park, N.C.

[21] Appl. No.: 824,218

[22] Filed: Aug. 12, 1977

[30] Foreign Application Priority Data

Aug. 13, 1976 [GB] United Kingdom .............. 33827/76
Apr. 21, 1977 [GB] United Kingdom .............. 16633/77

[51] Int. Cl.$^2$ ................. A61K 31/415; A61K 31/165
[52] U.S. Cl. ................................. 424/273 B; 424/324
[58] Field of Search ...................... 424/273, 273 B, 324

[56] References Cited

U.S. PATENT DOCUMENTS 3,929,821  12/1975  Beard et al. ..................... 424/273

OTHER PUBLICATIONS

Harfenist—Chem. Abst., vol. 77, (1972), p. 19404w.

*Primary Examiner*—Sam Rosen
*Attorney, Agent, or Firm*—Donald Brown

[57] ABSTRACT

A method of treating helminth infections in mammals comprising the concurrent or sequential administration of diamphenethide and oxfendazole.

30 Claims, No Drawings

TREATMENT OF HELMINTH INFECTIONS WITH OXFENDAZOLE AND DIAMPHENETHIDE, AND COMPOSITIONS THEREFOR

This invention relates to the treatment and prophylaxis of helminth infections and formulations for this purpose. In particular it provides a combination of active ingredients which has been found particularly efficacious against liver fluke and other helminth infections.

Animals are infected with liver fluke when eating forage contaminated with encysted forms of cercariae, an intermediate stage in the life-cycle of the fluke. The cercariae emerge from the cysts in the intestine of the host animal, penetrate the intestine wall, and make their way to the liver. At this stage they are microscopic in size, but grow as they wander around the liver parenchyma. This causes considerable destruction of the liver tissue and can give rise to the syndrome of acute fascioliasis which normally leads to death of the host when massive infections are present. If the animal survives, the flukes eventually reach the bile ducts where they mature into the adult worms. The presence of a massive infection in the bile ducts gives rise to the syndrome of chronic fascioliasis which is a serious debilitating disease of the host animal.

It is already known from U.K. Patent Specification No. 1,380,882 that the compound bis-(β-(4-acetamidophenoxy)ethyl)ether of formula (A),

hereinafter referred to as diamphenethide, is effective in combatting infections of Fasciola spp. especially in view of its high activity against immature fluke. However, in order to provide adequate control of infections of all ages a large dose is required, for example an oral dose of 120 mg/kg bodyweight is usually required in sheep.

Whilst it is suggested in U.K. Patent Specification No. 1,380,882 that a compound such as diamphenethide might be conveniently administered in conjunction with a benzimidazole anthelmintic such as Thiabendazole, Parbendazole or Cambendazole in order to supplement or complement its activity, none of these compounds has been found to improve the efficacy of diamphenethide, and in fact Thiabendazole at a dose of 50 mg/kg bodyweight was found to adversely affect the flukicidal activity of an identical dose of diamphenethide.

The compound methyl 5(6)-phenylsulphinylbenzimidazole-2-carbamate of formula (B),

hereinafter referred to as oxfendazole has previously been described in U.S. Pat. No. 3,929,821 and in J. Med. Chem., 18, 1164 (1975) as being effective against gastrointestinal nematodes in domestic animals at an oral dose of from 5 to 10 mg/kg bodyweight.

It has now been found that the minimum effective dose of diamphenethide may be considerably reduced upon concurrent or sequential administration with a relatively small amount of oxfendazole. Although oxfendazole exhibits weak activity against mature fluke when administered orally to sheep or cattle at a dose of 5 mg/kg bodyweight, it has been found completely inactive against immature fluke in either species.

It is therefore apparent that oxfendazole is capable of synergising the flukicidal activity of diamphenethide to provide a more efficacious flukicidal combination than might be expected from the separate activity of the components. Alternatively, oxfendazole may be regarded as providing an unexpected enhancement of the flukicidal activity of diamphenethide.

For example a dose of 120 mg/kg of diamphenethide is generally required to control fluke infections in sheep and even at this dose its activity against mature fluke (e.g. 12 week old) may be somewhat variable. At a dose of 50 mg/kg the activity of diamphenethide is substantially reduced and may effect less than 50% clearance of a fluke infection. Similarly, oxfendazole at a dose of 5 mg/kg is totally ineffective against immature fluke although a variable activity against mature fluke may be observed. However, a combined dose of 50 mg/kg diamphenethide together with 5 mg/kg oxfendazole has been found to effect substantially complete clearance of fluke infections regardless of the age of the fluke.

In addition to decreasing the total amount of drug given, a further advantage of combining diamphenethide with oxfendazole is that the combined product is effective against a broad spectrum of helminth infections. This is particularly convenient since in practice it is often found that fluke and other worm infections occur at approximately the same time, and the combined treatment requires only one dosing of each animal to control all of the infections.

A further surprising advantage of the present invention is that the simultaneous administration of oxfendazole has been found to reduce or eliminate certain toxic effects of diamphenethide which are manifested at doses higher than those used for therapeutic purposes.

In a combination of diamphenethide with oxfendazole for the control of fluke infections an appropriate amount of diamphenethide will generally lie in the range of from 20 to 100 mg/kg bodyweight and the amount of oxfendazole from 2.5 to 50 mg/kg bodyweight, although the amount of diamphenethide may be increased if desired. However the optimum effective dose will of course vary with the nature of the host and the severity, nature and age of the infection; but it has been found that in sheep the preferred dose is from 40 to 60, for example about 50 mg/kg bodyweight of diamphenethide with from 5 to 10, preferably about 5 mg/kg bodyweight of oxfendazole. In cattle, the preferred dose is from 60 to 100, for example 95 mg/kg diamphenethide with from 3 to 6, for example 3.75 mg/kg oxfendazole.

The compound oxfendazole is capable of forming acid addition salts for example with inorganic acids such as for example sulphuric, sulphonic, sulphamic, nitric, phosphoric and hydrochloric acids or organic acids such as for example acetic, citric, lactic, palmitic, tartaric, succinic, maleic and benzoic acids. Preferred salts are those which are pharmaceutically acceptable by which is meant those which do not unduly diminish the anthelmintic properties of the parent compound, and which are not injurious to the recipient thereof.

The combination of diamphenethide together with oxfendazole or a salt thereof (hereinafter referred to as the "Combination") may be administered to mammals to control fluke and nematode infections; and if administered concurrently the Combination may take the form of a simple mixture of ingredients, separate formulations of each ingredient or a single formulation of both ingredients.

Such a Combination may be used for the treatment or prophylaxis of F. hepatica infections in ruminants including sheep, cattle, goat, buffalo and horse; and F. gigantica in mice and ruminants including sheep, buffalo and cattle. The Combination will also control gastrointestinal nematode infections which the host may also possess.

For the purpose of controlling helminth infections the Combination conveniently comprises diamphenethide and oxfendazole or a salt thereof in the proportion of from 1:1 to 50:1 and preferably from 5:1 to 30:1 for example about 10:1 and about 26.25:1.

Although the Combination may be administered as a mixture of the raw chemicals, it is preferably formulated together in the customary compositions which additionally contain one or more inert carrier materials commonly used in veterinary compositions as a vehicle for active ingredients.

The compositions may take the form of discrete units such as boluses or pellets each containing a predetermined amount of the active ingredient.

For example unit dose compositions of the Combination may comprise upto 15 g. of the Combination but generally smaller units are used. For example boluses for administration to cattle conveniently contain from 2 to 12 and preferably about from 7 to 10 g. of the Combination, whereas boluses for administration to sheep contain upto 4, for example from 1 to 3 g. of the Combination. Such boluses in addition may comprise the usual excipients such as diluents, disintegrating agents, surface active agents and lubricants.

Alternatively the Combination may be presented as a solution or suspension in a water-in-oil liquid emulsion, for example as a liquid drench. Such compositions may additionally contain such other conventional agents as preservatives, thickening agents, wetting and dispersing agents, buffers, humectants, emulsifying agents, fillers, emoluents and surface active agents.

The Combination may further be presented as a powder or granules, an electuary or paste, in salt licks or block licks or in the feed or as a feed supplement intended for the host animal, for example as a premix.

The compositions may be made by any of the methods of pharmacy but all methods include the step of bringing into association by admixture the Combination with the carrier which constitutes one or more accessory ingredients. In general the compositions are prepared by uniformly and intimately bringing into association the active ingredient with liquid carriers or finely divided solid carriers or both, and then, if necessary, shaping the product into the desired composition. The compositions contain one or more of the usual accessory ingredients used to prepare veterinary compositions.

Any method known in the art may be used for the synthesis of diamphenethide and oxfendazole, for example those described in U.K. Patent Specification No. 1,380,882 and U.S. Pat. No. 3,929,821, the contents of which specifications are hereby incorporated by reference.

The present invention therefore comprises in summary the following aspects which we will claim, but the following aspects are not intended to be exhaustive:

(a) The combination of oxfendazole or a salt thereof and diamphenethide;

(b) An anthelmintic composition containing a liver fluke and nematode effective toxic amount of the Combination;

(c) A method for controlling fluke infections in a mammal comprising the concurrent or sequential administration of a non-toxic flukicidal amount of diamphenethide and oxfendazole or a salt thereof.

(d) A method for controlling helminth infections in a mammal comprising the concurrent or sequential administration of a non-toxic anthelmintic amount of diamphenethide and oxfendazole or a salt thereof.

The present invention is illustrated by the following examples which are not to be construed as a limitation thereof.

EXAMPLE 1

Treatment of F. Hepatica Infection in Sheep

Sheep were experimentally infected with F. hepatica by giving each animal about 200 metacercariae in water by drenching bottle. At a specified time after commencement of the infection each sheep, other than controls, was treated with diamphenethide, oxfendazole or a combination of the two, and two weeks after treatment the sheep were slaughtered and examined for the presence of fluke. Details of the age of fluke infection, treatment and the efficacy of the treatment (expressed as percentage reduction in the number of flukes which were found as compared with untreated controls) are given in Table 1.

TABLE 1

| Age of fluke (weeks) | No. in group | Oxfendazole mg/kg | Diamphenethide mg/kg | Efficacy % |
|---|---|---|---|---|
| 1 | 2 | 5 | 50 | 100 |
|   | 2 | 5 | 25 | 100 |
|   | 1 | 5 | 0 | 0 |
|   | 1 | 0 | 50 | 100 |
| 3 | 2 | 5 | 50 | 100 |
|   | 1 | 5 | 25 | 59 |
|   | 1 | 5 | 0 | 0 |
| 4 | 2 | 5 | 50 | 100 |
|   | 2 | 5 | 25 | 0 |
|   | 1 | 5 | 0 | 67 |
|   | 1 | 0 | 50 | 97 |
| 7 | 2 | 5 | 50 | 93 |
|   | 2 | 5 | 25 | 57 |
|   | 1 | 5 | 0 | 17 |
|   | 1 | 0 | 50 | 83 |
| 10 | 2 | 5 | 50 | 57 |
|   | 2 | 5 | 25 | 62 |
|   | 1 | 5 | 0 | 30.5 |
|   | 1 | 0 | 50 | 44 |
| 12 | 4 | 5 | 50 | 97 |
|   | 4 | 5 | 0 | 83 |
|   | 4 | 0 | 50 | 44 |

EXAMPLE 2

Treatment of F. Hepatica Infection in Cattle

In a similar manner to that described in Example 1 the efficacy of oxfendazole/diamphenethide combinations were assessed in cattle and the results expressed in Table 2.

Table 2

| Age of fluke (weeks) | No. in group | Oxfendazole mg/kg | Diamphenethide mg/kg | Efficacy % |
|---|---|---|---|---|
| 6 | 2 | 5 | 50 | 85 |
|   | 1 | 5 | 0 | 47 |
|   | 3 | 2.5 | 50 | 8 |
| 12 | 3 | 5 | 70 | 92 |
|   | 3 | 5 | 0 | 39 |
|   | 3 | 2.5 | 95 | 63 |
| 13 | 3 | 5 | 50 | 78 |
| 14 | 3 | 5 | 70 | 93 |

In the following examples, provided to illustrate veterinary compositions of the present invention, the following substances are used:

Bevaloid dispersant: a naphthalene formaldehyde sulphonic acid condensate;
Keltrol F: xanthan gum, polysaccharide B-1459;
Aerosol OT: dioctyl sodium sulfosuccinate;
Myrj 52 (Trade Name): Polysorbate 60, a polyoxyethylene derivative of fatty acid;
Ethylan KEO: an ethyleneoxide nonylphenyl condensate;
Neosyl: a fine silica filler;
Natrosol 250: hydroxyethylcellulose.

EXAMPLE A

| LIQUID DRENCH | | SHEEP | CATTLE |
|---|---|---|---|
| (a) | Oxfendazole | 1.5 | 0.80 |
|   | Diamphenethide | 15.0 | 21.00 |
|   | Bevaloid Dispersant | 1.00 | 1.00 |
|   | Sodium Benzoate | 1.00 | 1.00 |
|   | Thymol | 0.04 | 0.04 |
|   | Bentonite | 3.00 | 3.00 |
|   | Water | 78.46 | 73.16 |
|   |   | 100.00% | 100.00% |
| (b) | Oxfendazole | 1.50 | 0.8 |
|   | Diamphenethide | 15.00 | 21.0 |
|   | Sorbic Acid | 0.50 | 0.50 |
|   | Citric Acid | 0.40 | 0.40 |
|   | Sodium citrate | 0.90 | 0.90 |
|   | Keltrol | 0.10 | 0.10 |
|   | Aerosol OT | 0.15 | 0.15 |
|   | Water | 81.45 | 76.15 |
|   |   | 100.00% | 100.00% |
| (c) | Oxfendazole | 1.5 | 0.8 |
|   | Diamphenethide | 15.0 | 21.0 |
|   | Myrj 52 | 2.5 | 2.5 |
|   | Parachlorometacresol | 0.2 | 0.2 |
|   | Sodium carboxymethyl cellulose | 0.8 | 0.8 |
|   | Water | 80.0 | 74.7 |
|   |   | 100.00% | 100.00% |

EXAMPLE B

| PASTE | | SHEEP | CATTLE |
|---|---|---|---|
| (a) | Diamphenethide | 60.0 w/w | 63.00 w/w |
|   | Oxfendazole | 6.00 | 2.40 |
|   | Glycerin | 3.30 | 3.30 |
|   | Ethylan KEO | 2.00 | 2.00 |
|   | Natrosol 250 | 0.20 | 0.20 |
|   | Nipagin M | 0.10 | 0.10 |
|   | Sorbitan monooleate | 0.40 | 0.40 |
|   | Cetostearyl alcohol | 3.50 | 3.50 |
|   | Mineral oil | 13.00 | 13.00 |
|   | Water | 11.50 | 12.10 |
|   |   | 100.00% | 100.00% |
| (b) | Diamphenethide | 50.00 | 52.50 |
|   | Oxfendazole | 5.00 | 2.00 |
|   | Bevaloid dispersant | 0.40 | 0.40 |
|   | Glycerin | 8.60 | 8.60 |
|   | Gum Tragacanth | 1.80 | 1.80 |
|   | Thymol | 0.04 | 0.04 |
|   | Water | 34.16 | 34.66 |
|   |   | 100.00% | 100.00% |
| (c) | Diamphenethide | 25.00 | 26.25 |
|   | Oxfendazole | 2.50 | 1.00 |
|   | Bevaloid dispersant | 1.00 | 1.00 |
|   | Glycerin | 23.00 | 23.00 |
|   | Parachlorometacresol | 0.20 | 0.20 |
|   | Neosyl | 15.00 | 15.00 |
|   | Keltrol | 0.50 | 0.50 |
|   | Water | 32.80 | 33.05 |
|   |   | 100.00% | 100.00% |
| (d) | Diamphenethide | 20.00 | 10.5 |
|   | Oxfendazole | 2.00 | 0.40 |
|   | Petroleum Jelly | 10.00 | 20.00 |
|   | Mineral Oil | 50.00 | 40.00 |
|   | Kaolin BP | 18.00 | 29.10 |
|   |   | 100.00% | 100.00% |

EXAMPLE C

| PREMIX | | | | | |
|---|---|---|---|---|---|
| (a) | Oxfendazole | 1 w/w | 7 w/w | 3.2 w/w | 0.4 w/w |
|   | Diamphenethide | 10 | 70 | 84.0 | 10.5 |
|   | Maize Meal | 89 | 23 | 12.8 | 89.1 |
|   |   | 100 % | 100 % | 100.0 % | 100.0 % |
| (b) | Oxfendazole | 1 | 7 | 3.2 | 0.4 |
|   | Diamphenethide | 10 | 70 | 84.0 | 10.5 |
|   | Calcium carbonate | 89 | 23 | 12.8 | 89.1 |
|   |   | 100 % | 100 % | 100.0 % | 100.0 % |

What I claim is:

1. An anthelmintic combination comprising effective amounts of diamphenethide in association with oxfendazole or an acid addition salt thereof.

2. A combination of claim 1 comprising an effective flukicidal amount of a combination as claimed in claim 1.

3. A combination as claimed in claim 1 wherein the ratio of diamphenethide to oxfendazole is in the range of from 1:1 to 50:1.

4. A combination as claimed in claim 3 wherein the ratio is from 5:1 to 30:1.

5. A combination as claimed in claim 4 wherein the ratio is 10.1.

6. A combination as claimed in claim 4 wherein the ratio is 26.25:1.

7. A composition suitable for use in the treatment of liver fluke infection in a mammal comprising a combination as claimed in claim 1 in association with an inert carrier.

8. A composition as claimed in claim 7 suitable for oral administration.

9. A composition as claimed in claim 7 comprising from 5 to 95% by weight of the combination.

10. A composition as claimed in claim 7 wherein the carrier includes a solid diluent.

11. A composition as claimed in claim 7 wherein the carrier includes a liquid diluent.

12. A composition as claimed in claim 7 wherein the carrier includes at least one substance selected from dispersing agents, wetting agents, suspending agents, gelling agents and thickening agents.

13. A composition as claimed in claim 7 wherein the carrier includes at least one substance selected from surface active agents, diluents, disintegrating agents, lubricants, preservatives, buffers, humectants, emulsifying agents, fillers and emoluents.

14. A composition as claimed in claim 7 in the form of a pellet.

15. A composition as claimed in claim 7 in the form of a bolus.

16. A composition as claimed in claim 7 in the form of a paste.

17. A composition as claimed in claim 7 in the form of a liquid drench.

18. A composition as claimed in claim 7 when incorporated into animal feedstuff or a permix therefor.

19. A composition as claimed in claim 7 in the form of a unit dose comprising up to 15 grammes of the combination.

20. A composition as claimed in claim 19 comprising from 0.5 to 10 grammes of the combination.

21. An anthelmintic combination comprising effective amounts of diamphenethide in association with oxfendazole.

22. A veterinary composition for use in the treatment of helminth infections which comprises diamphenethide or a pharmaceutically acceptable salt thereof and oxfendazole, the amount of oxfendazole being at least sufficient to enhance the activity of diamphenethide or the salt thereof.

23. A method of treating a fluke infection in a mammal comprising the administration to said mammal of an effective flukicidal amount of diamphenethide and oxfendazole or a salt thereof which may be presented concurrently or sequentially.

24. A method as claimed in claim 23 wherein the oxfendazole or a salt thereof and diamphenethide are administered concurrently.

25. A method as claimed in claim 23 comprising the administration of an effective flukicidal amount of diamphenethide and oxfendazole or an acid addition salt thereof.

26. A method as claimed in claim 23 which comprises administration of from 20 to 100 mg/kg bodyweight diamphenethide and from 2.5 to 50 mg/kg bodyweight oxfendazole.

27. A method as claimed in claim 23 for treating a fluke infection in sheep which comprises administration of from 40 to 60 mg/kg bodyweight diamphenethide with from 2.5 to 10 mg/kg bodyweight oxfendazole.

28. A method as claimed in claim 23 for treating a fluke infection in cattle which comprises administration in the range of from 60 to 100 mg/kg bodyweight diamphenethide with from 3 to 6 mg/kg oxfendazole.

29. A method as claimed in claim 23 wherein the diamphenethide and oxfendazole are administered orally.

30. A method of treating a liver fluke infection in a mammal comprising the administration to the mammal having said infection an anthelmintic combination comprising effective amounts of diamphenethide in association with oxfendazole or an acid addition salt thereof.

* * * * *